United States Patent [19]
Grabenkort et al.

[11] Patent Number: 5,125,911
[45] Date of Patent: Jun. 30, 1992

[54] SPIKE HOLDER

[76] Inventors: Richard W. Grabenkort, 102 Carriage Rd., Barrington, Ill. 60010; William L. Rudzena, 1317 W. Channel Beach, McHenry, Ill. 60050

[21] Appl. No.: 483,195

[22] Filed: Feb. 20, 1990

[51] Int. Cl.⁵ .............................................. A61M 5/00
[52] U.S. Cl. .................................. 604/250; 604/256; 604/34; 128/912; 248/81; 81/9.3
[58] Field of Search ............... 604/403, 134, 411, 414, 604/256, 263, 250, 322–333, 29, 34; 128/912; 24/489, 19, 205; 222/74, 555, 548; 248/62, 63, 139, 81; 81/9.3

[56] References Cited

U.S. PATENT DOCUMENTS

| | | | |
|---|---|---|---|
| 707,234 | 8/1902 | Jones | 24/489 |
| 2,722,932 | 11/1955 | Hickey | 604/34 |
| 3,720,979 | 3/1973 | Krawagna | 24/489 |
| 4,192,304 | 3/1980 | Millet | 604/250 |
| 4,405,315 | 9/1983 | Handt | 604/29 |
| 4,463,482 | 8/1984 | Hawie | 24/489 |
| 4,557,727 | 12/1985 | Handt | 604/29 |
| 4,736,925 | 4/1988 | Kamstrup-Larsen et al. | 604/323 |
| 4,840,621 | 6/1989 | Larkin et al. | 604/29 |

Primary Examiner—C. Fred Rosenbaum
Assistant Examiner—Chalin Smith

[57] ABSTRACT

For use in preventing spillage in a continuous ambulatory peritoneal dialysis apparatus, a two-part spike holder which automatically occludes a flexible tubing connected to the hollow spike as the spike is mounted in the holder, the two parts of the spike holder being pivotally interconnected and biased toward one another.

3 Claims, 3 Drawing Sheets

SPIKE HOLDER

BACKGROUND OF THE INVENTION

This invention relates to the field of medical devices and, more particularly, to a continuous ambulatory peritoneal dialysis apparatus (CAPD) wherein a piercing pin or spike of a tube set connected to a container of used dialysis solution is automatically transferred from the clamped port of the container of used solution to the clamped port of a container of fresh dialysis solution with a minimum of spillage of the used dialysis solution in the CAPD apparatus.

One such CAPD apparatus is disclosed in U.S. Pat. No. 4,840,621 which issued Jun. 20, 1989 to the same assignee to whom this application is assigned. To provide an appropriate structural and environmental background for the invention disclosed and claimed herein, the disclosure of said U.S. Pat. No. 4,840,621 is incorporated herein by reference. After a CAPD patient has opened the appropriate clamping devices to permit a used charge of dialysis solution to drain by gravity from his or her peritoneal cavity into an empty container, the port of the used solution container is clamped and mounted in the CAPD apparatus with the spike of the tube set, which is still sealingly mounted in the port of the used solution container, being mounted in a spike holder or cradle of the CAPD apparatus. Upon activation of the motor of the CAPD apparatus, the spike holder and the spike mounted thereon are automatically, by means of a unique transfer mechanism, linearly withdrawn from the clamped port of the used solution container, rotated through 180 degrees, and then linearly moved into seal piercing engagement in a clamped port of a container of fresh dialysis solution.

It is important that the tube set attached to the spike be occluded or otherwise clamped closed as close as possible to the spike prior to the spike being withdrawn from the clamped port of the used solution container to prevent spillage or even flooding of the CAPD apparatus by used solution remaining in the tube set. Although mechanical clamping devices may be provided on the tube set, many patients undergoing continuous ambulatory peritoneal dialysis may be so impaired by failing eyesight, by lessening of their physical strength and dexterity, or by simple forgetfulness that such clamping devices may not be properly activated prior to activation of the CAPD apparatus. It is noted that it may be necessary for a CAPD patient to drain and recharge his or her peritoneal cavity with fresh dialysis solution as often as four times a day so the procedure must be as simple and accident-proof as possible.

SUMMARY OF THE INVENTION

The present invention is directed to a new and improved spike holder or cradle whereby the simple act of mounting the spike therein provides automatic occlusion of the tube set attached to the spike and thus insures against spillage of used dialysis solution into the CAPD apparatus from the tube set upon actuation of the CAPD apparatus.

The unique spike holder of the present invention is characterized by a pivotally interconnected two part housing, each part having mounting means thereon for either the tip or rear end of the spike whereupon the spike is mountable therebetween, spring means serving to bias the two housing parts together. The mounting means for the rear end of the spike is in the form of a relatively close fitting well whereupon the tube set which projects from the rear end of the spike is automatically occluded as the spike is mounted in the two part holder.

Objects and advantages of the present invention will be apparent from the following description.

DETAILED DESCRIPTION OF THE PREFERRED EMBODIMENT

Figure 1:
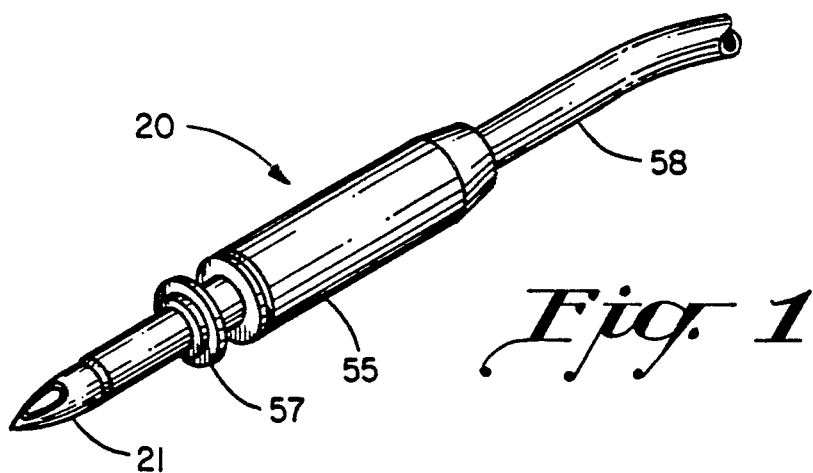
FIG. 1 is a perspective view of a hollow spike connected to the end of a CAPD tube set, which spike is to be mounted in the two-part spike holder of the present invention.

With reference to FIG. 1 of the drawings, the hollow spike or piercing pin 20 of the continuous ambulatory peritoneal dialysis apparatus (CAPD) of U.S. Pat. No. 4,840,621, which issued Jun. 20, 1989, to the same assignee to whom this application is assigned, the disclosure of which is incorporated herein by reference, is characterized by a main body portion 55, a sharpened tip 21 which projects forwardly from the body portion 55, by an annular flange 57 on the tip 21 which is spaced forwardly of the front end of the body portion 55, and by a flexible tubing 58 of a dialysis tube set 31 which is connectable to a patient's in-place peritoneal catheter.

Figure 2:
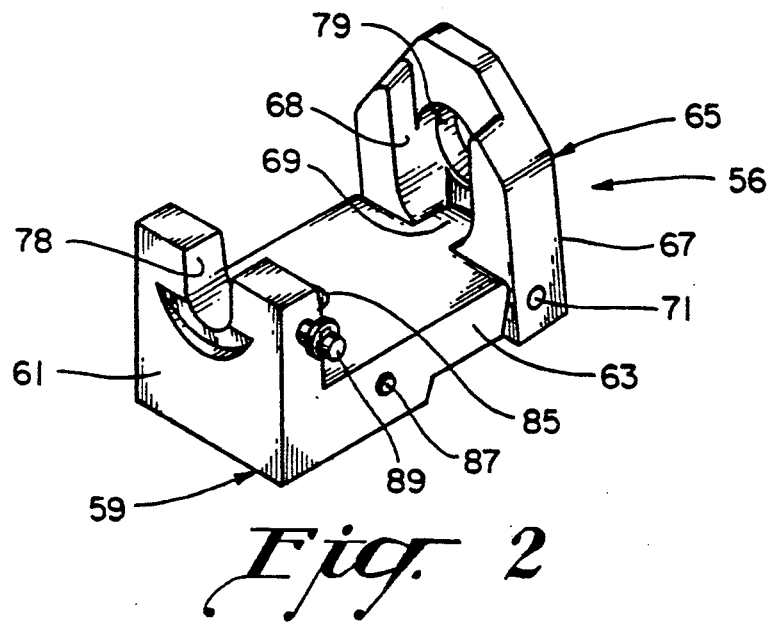
FIG. 2 is a perspective view of the two-part spike holder of the present invention.
Figure 3:
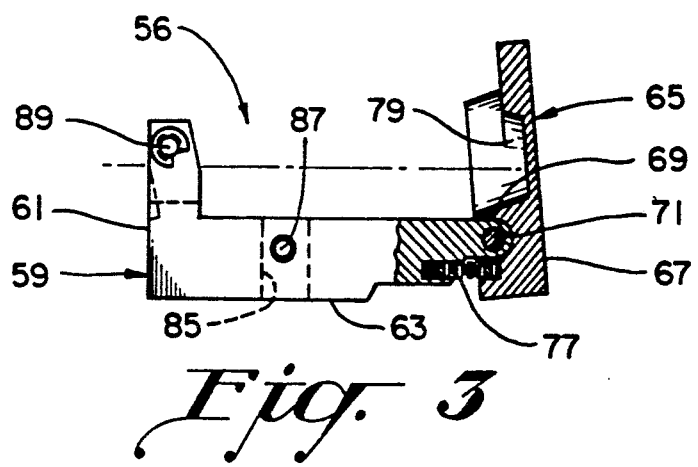
FIG. 3 is a side elevational view partially in vertical section of the spike holder shown in FIG. 2.
Figure 4:
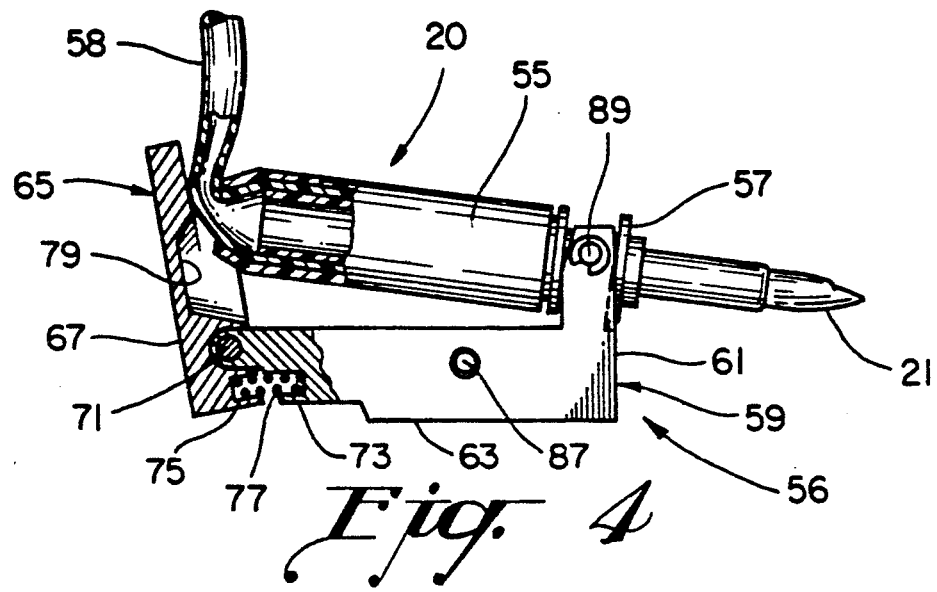
FIG. 4 is an opposite side elevational view partially in vertical section and illustrating mounting of the spike shown in FIG. 1 in the spike holder shown in FIGS. 2 and 3.

An improved, self-clamping spike holder or carrier 56 of the present invention is shown in FIGS. 2 and 3. This holder 56 for the hollow spike 20 of FIG. 1 has two pivotally interconnected housing parts, a right angular front part 59 which is characterized by an upstanding front wall 61 and a rearwardly extending bottom wall 63 and a rear part 65 which is the form of an upstanding rear wall 67 which is characterized by a vertically extending, forwardly facing slot 68.

The bottom wall 63 of the front housing part 59 has a rearwardly projecting tongue 69 which fits into the lower end of the slot 68 in the rear housing port 65 with a pivot pin 71 extending through the lower portion of the rear housing part 65 and the tongue 69 whereby to pivotally interconnect the two housing parts 59 and 65. A pair of bore-like spring sockets 73 are provided in the rear face of the bottom wall 63 of the front housing part 59 on either side of the tongue 69 with aligned bore like spring sockets 75 being provided in front surface of the rear wall 67 on either side of the slot 68. A pair of coil springs 77 are seated one in each set of aligned sockets 73, 75 whereby to bias the rear housing port 65 counterclockwise about the pivot pin 71 relative to the front housing port 59, the top of the rear wall 67 being biased toward the top of the front wall 61.

Mounting means for the spike 20 are provided on the front housing part 59 in the form of an upwardly opening U-shaped slot or notch 78 and on the rear housing part 65 in the form of a recess or well 79 which is just slightly larger than the rear end of the main body portion 55 of the spike 20. The tip 21 of the spike 20 is seated in the U shaped notch 78 with the annular flange 57 engageable with the forwardly facing edge of the notch 78 and with the front end of the main body portion 55 engageable with the rearwardly facing edge of the notch 78, as if it were a second flange spaced rearwardly of the flange 57.

Figure 5:
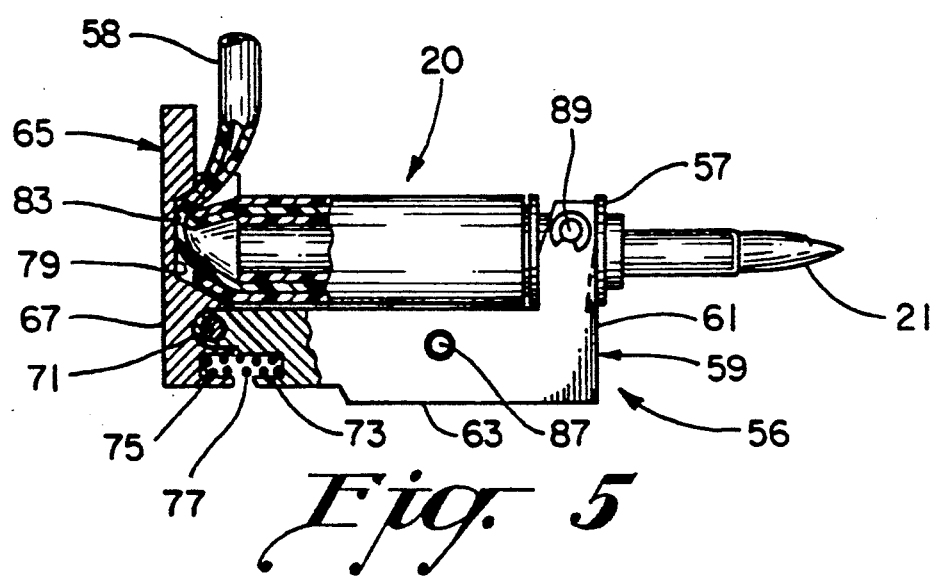
FIG. 5 is a view similar to FIG. 4 after completion of the mounting of the spike in the spike holder.
Figure 6:
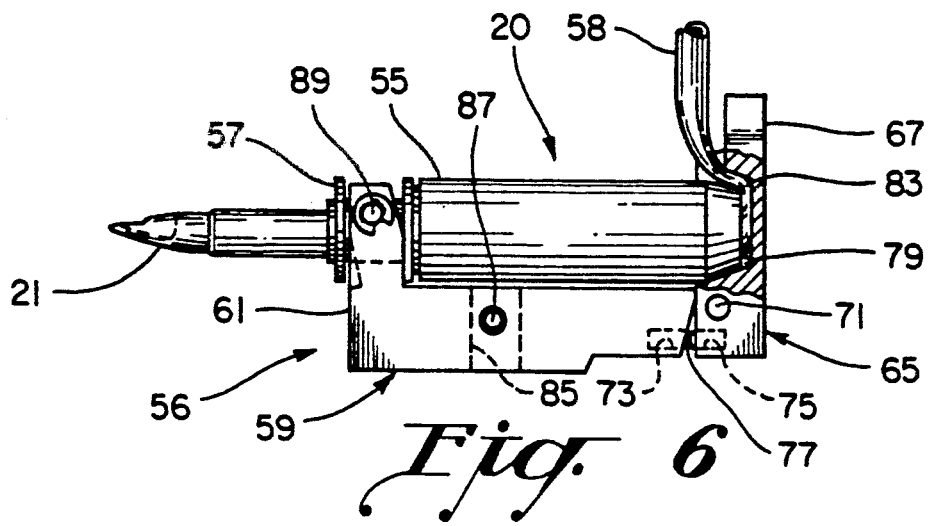
FIG. 6 is a side elevational view partially in vertical section of the spike shown in FIG. 1 mounted in the spike holder shown in FIGS. 2 and 3.
Figure 7:
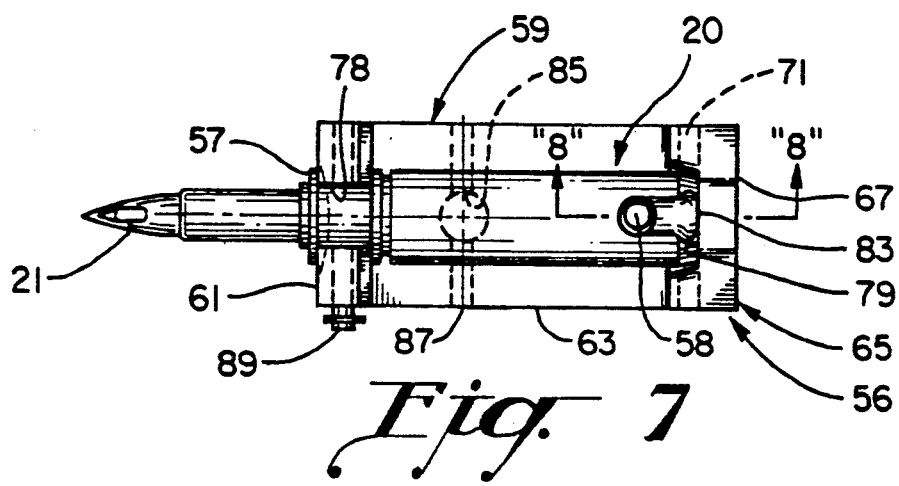
FIG. 7 is a top plan view of FIG. 6.
Figure 8:
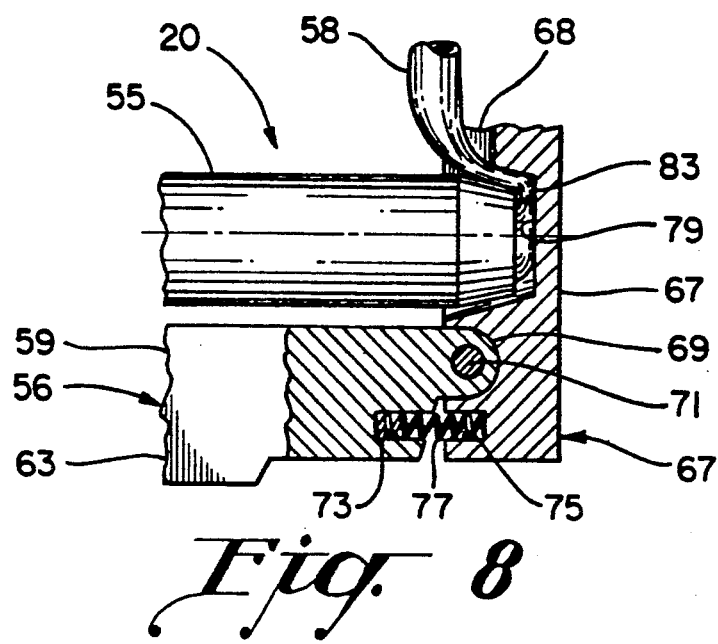
FIG. 8 is an enlarged fragmentary view partially in vertical section taken generally along line 8—8 of FIG. 7.

As best illustrated in FIG. 5, mounting of the spike 20 in the spike holder or carrier 50 automatically occludes or otherwise clamps closed the tubing 58 (as at 83) and thus insures against spillage of any used dialysis solution from the tubing set 31 into the piercing pin transfer device of U.S. Pat. No. 4,840,621 which is incorporated herein, even if the patient effecting the solution container transfer neglected to activate other tube clamping devices provided on the tubing set 31.

The bottom wall 63 of the front housing part is provided with a vertical bore 85 so that the spike holder 50 can be mounted on the upper end of the vertical shaft 80, of the piercing pin transfer device of U.S. Pat. No. 4,840,621 which is incorporated herein for rotation and linear movement therewith during the transfer operation. Locking means 87 may be provided for securing the spike holder 50 to the vertical shaft 80.

Associated with the U-shaped notch 78 is a microswitch actuator 89 to insure that the piercing pin transfer device of U.S. Pat. No. 4,840,621 which is incorporated herein may be activated only if the spike 20 is properly mounted in the spike holder 50. It is noted that although applicant's invention is described herein in the environment of its current preferred embodiment, the basic new and novel two-part spike holder disclosed and shown in the drawings, which has as one of its new and novel features the automatic occlusion of a tubing projecting from the rear end of a spike upon mounting of the spike in the holder, is not limited in its usage to this preferred embodiment described herein, that is, in a continuous ambulatory peritoneal dialysis apparatus. Several other situations can be contemplated wherein a spike having a tubing extending from its rear end is to be mounted in a holder, temporarily or otherwise, and, if connected in a fluid delivery or drainage system, with the tubing to be automatically clamped shut to prevent leakage of the fluid from the spike. Applicant's claimed spike holder would clearly be perfect for such situations.

Although the present invention has been described in connection with a presently preferred embodiment, those skilled in the art will recognize many modifications which cn be used in the practice of the invention without departing from its scope. It is intended that such changes and modifications be covered by the following claims.

We claim:

1. A tube-clamping spike holder for a hollow spike having a pointed front end and a flexible tube extending from the rear end thereof, said holder comprising front and rear portions pivotally connected together with said hollow spike being received therebetween, spring means biasing said front and rear portions toward one another, means on said front portion engaged with said front end of said hollow spike, and a forwardly facing well formed in said rear portion receiving the rear end of said hollow spike with said flexible tube being automatically clamped closed by portions of said well upon insertion of said rear end of said hollow spike into said well.

2. The spike holder of claim 1 wherein said front end of said hollow spike is provided with spaced apart radial flanges and wherein said front portion of said holder is provided with an upwardly opening slot receiving said front end of said hollow spike with said pair of flanges engaging oppositely-facing edges of said slot.

3. An automatic flexible-tube-clamping cradle for a hollow spike having a pointed front end and a flexible tubing extending from the rear end thereof, said cradle comprising a two-part housing characterized by a front end portion having a notch receiving the front end of the hollow spike and by a rear end portion pivotally connected to said front end portion and having a generally circular recess receiving the rear end of said hollow spike with the tubing extending from the rear end thereof being automatically clamped closed by the edge of said circular recess, and spring means biasing said rear end portion toward said front end portion to maintain said clamping of said flexible tubing.

* * * * *

UNITED STATES PATENT AND TRADEMARK OFFICE
CERTIFICATE OF CORRECTION

PATENT NO. : 5,125,911

DATED : June 30, 1992

INVENTOR(S) : Richard W. Grabenkort, William L. Rudzena

It is certified that error appears in the above-identified patent and that said Letters Patent is hereby corrected as shown below:

Column 1, line 63
Delete "two part" and insert --two-part--

Column 2, line 1
Delete "close fitting" and insert --close-fitting--

Column 3, line 9
Delete "U shaped" and insert --U-shaped--

Column 4, line 10
Delete "cn" and insert --can--

Column 4, line 22
Delete "forwardly facing" and insert --forwardly-facing--

Column 4, line 29
Delete "spaced apart" and insert --spaced-apart--

Signed and Sealed this

Thirty-first Day of August, 1993

Attest:

BRUCE LEHMAN

*Attesting Officer*   *Commissioner of Patents and Trademarks*